United States Patent
Asai et al.

(10) Patent No.: US 10,597,625 B2
(45) Date of Patent: Mar. 24, 2020

(54) PERFUSION CULTURE APPARATUS AND PERFUSION CULTURE METHOD

(71) Applicant: TAKASAGO ELECTRIC, INC., Nagoya-shi, Aichi (JP)

(72) Inventors: Naoya Asai, Nagoya (JP); Yuki Tsukamoto, Nagoya (JP)

(73) Assignee: TAKASAGO ELECTRIC, INC., Nagoya (JP)

( * ) Notice: Subject to any disclaimer, the term of this patent is extended or adjusted under 35 U.S.C. 154(b) by 0 days.

(21) Appl. No.: 15/787,364

(22) Filed: Oct. 18, 2017

(65) Prior Publication Data

US 2018/0112171 A1 Apr. 26, 2018

(30) Foreign Application Priority Data

Oct. 20, 2016 (JP) ................. 2016-206231

(51) Int. Cl.
| | | |
|---|---|---|
| *C12M 1/00* | (2006.01) | |
| *C12M 1/12* | (2006.01) | |
| *C12M 1/34* | (2006.01) | |
| *C12M 1/36* | (2006.01) | |

(52) U.S. Cl.
CPC ............ *C12M 29/10* (2013.01); *C12M 23/04* (2013.01); *C12M 25/04* (2013.01); *C12M 41/00* (2013.01); *C12M 41/32* (2013.01); *C12M 41/48* (2013.01)

(58) Field of Classification Search
CPC ..................................................... C12M 23/04
See application file for complete search history.

(56) References Cited

U.S. PATENT DOCUMENTS

2015/0072401 A1   3/2015 Nozaki et al.

FOREIGN PATENT DOCUMENTS

| JP | 2003-289851 A | 10/2003 |
|---|---|---|
| JP | 2008-086264 A | 4/2008 |
| JP | 2014-113118 A | 6/2014 |
| JP | 5866006 B2 | 2/2016 |
| JP | 2016-131551 A | 7/2016 |
| JP | 5960256 B2 | 8/2016 |
| JP | 2017-079633 A | 5/2017 |
| WO | 2013/175580 A1 | 11/2013 |
| WO | 2013/183121 A1 | 12/2013 |

OTHER PUBLICATIONS

Tanny et al. Applied and Environmental Microbiology, 1980, 40(2):269-273.*

"Suitable for 3D tissue cultivation"; Takasago-Fluidics, uploaded Jan. 24, 2016; (http://www.takasago-fluidics.com/news/2016/01/2423/).

* cited by examiner

*Primary Examiner* — Ben Shen

(74) *Attorney, Agent, or Firm* — Oliff PLC

(57) ABSTRACT

A perfusion culture apparatus, capable of culturing cells having a multilayer structure, includes (i) a film, which is a sheet-shaped carrier on which cells are seeded in a state in which a liquid medium is allowed to pass through the sheet-shaped carrier; (ii) a vessel, which holds the film in a state in which the liquid medium is in contact with front and rear surfaces of the film; and (iii) a gas chamber, which applies pressure from outside to the liquid medium on the side in contact with either of the front and rear surfaces of the film to form a pressure difference between the liquid medium on the side in contact with the one surface and the liquid medium on the side in contact with the other surface, the liquid medium passing through the film in accordance with the pressure difference.

8 Claims, 7 Drawing Sheets

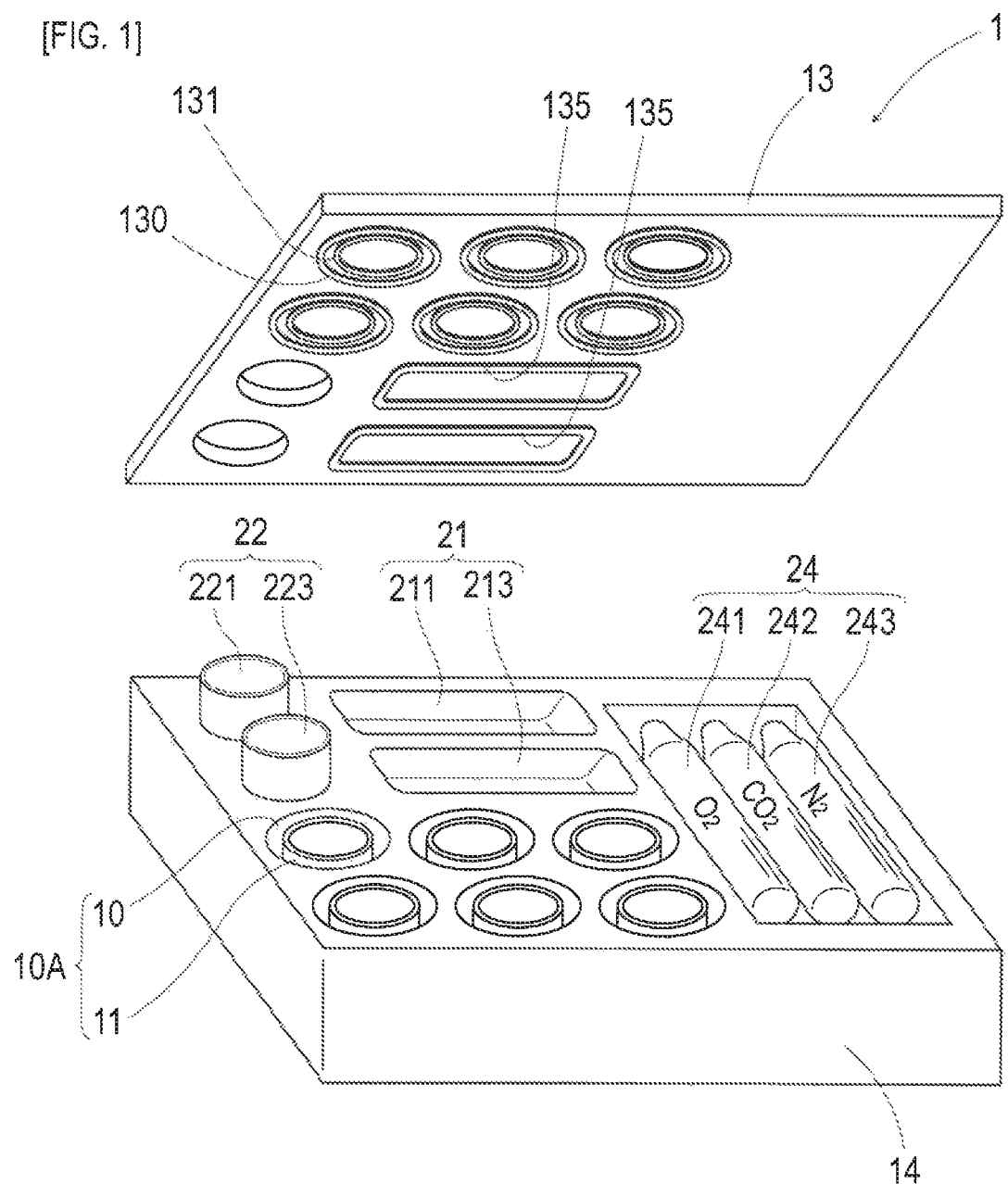

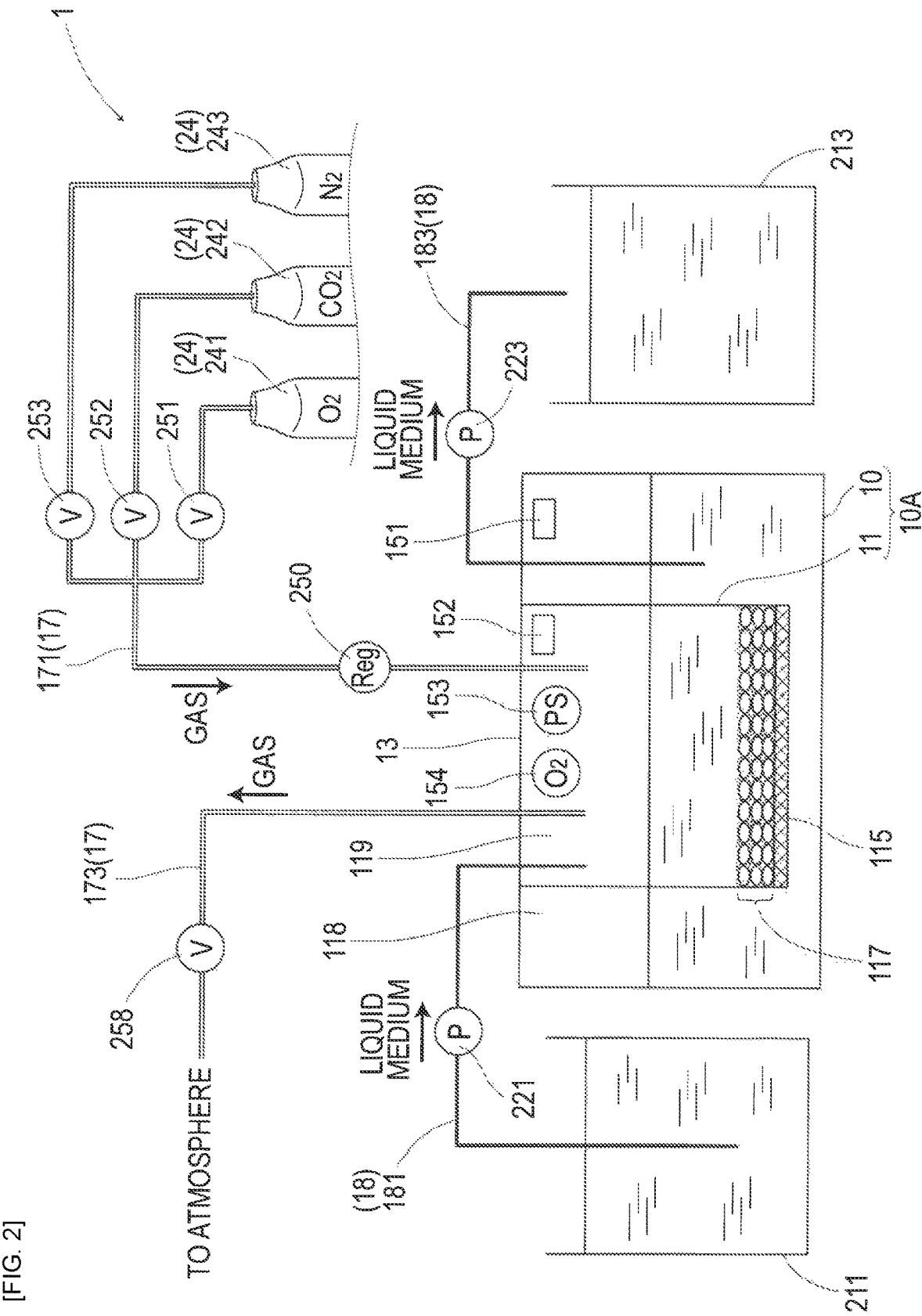
[FIG. 2]

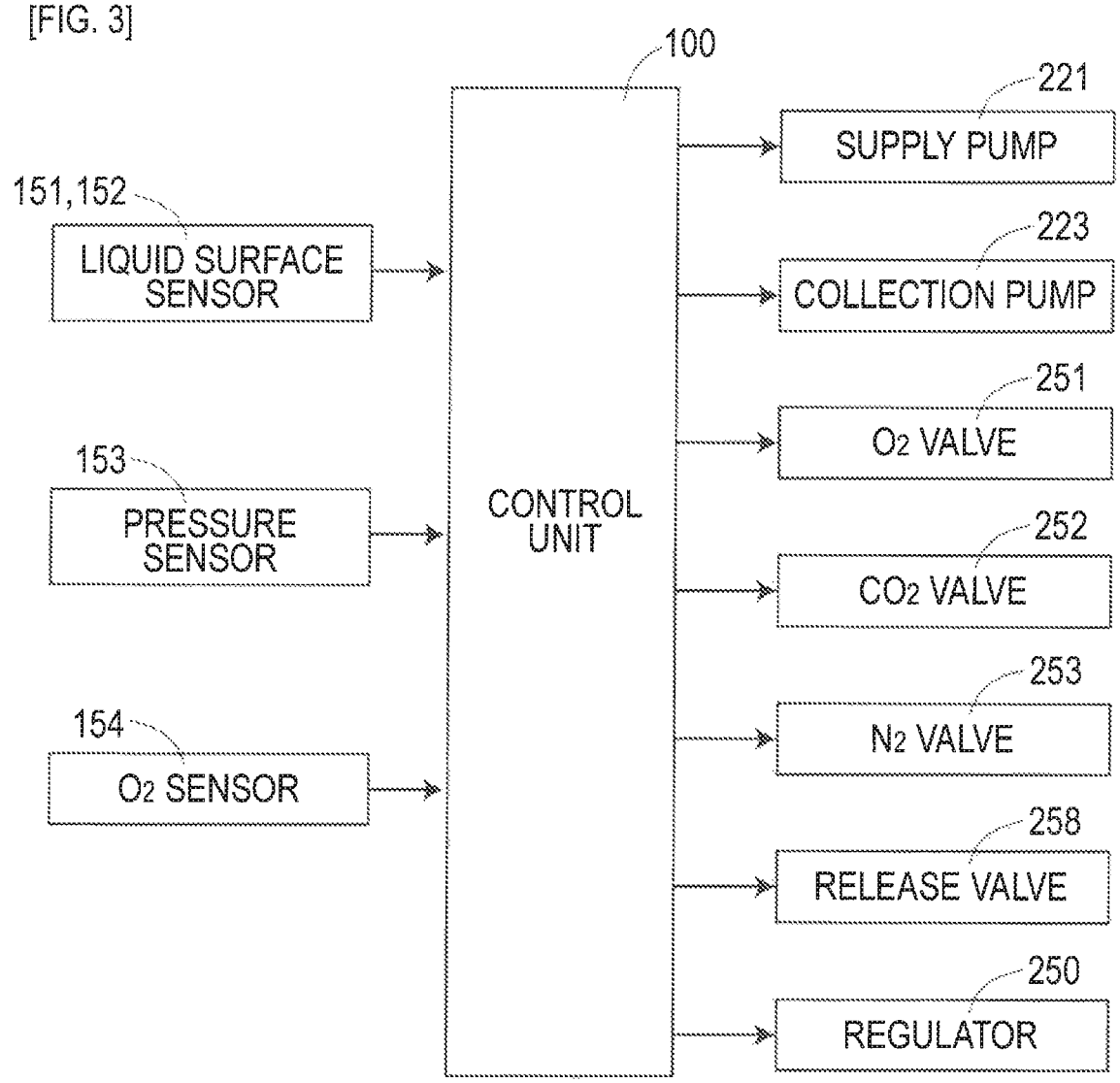
[FIG. 3]

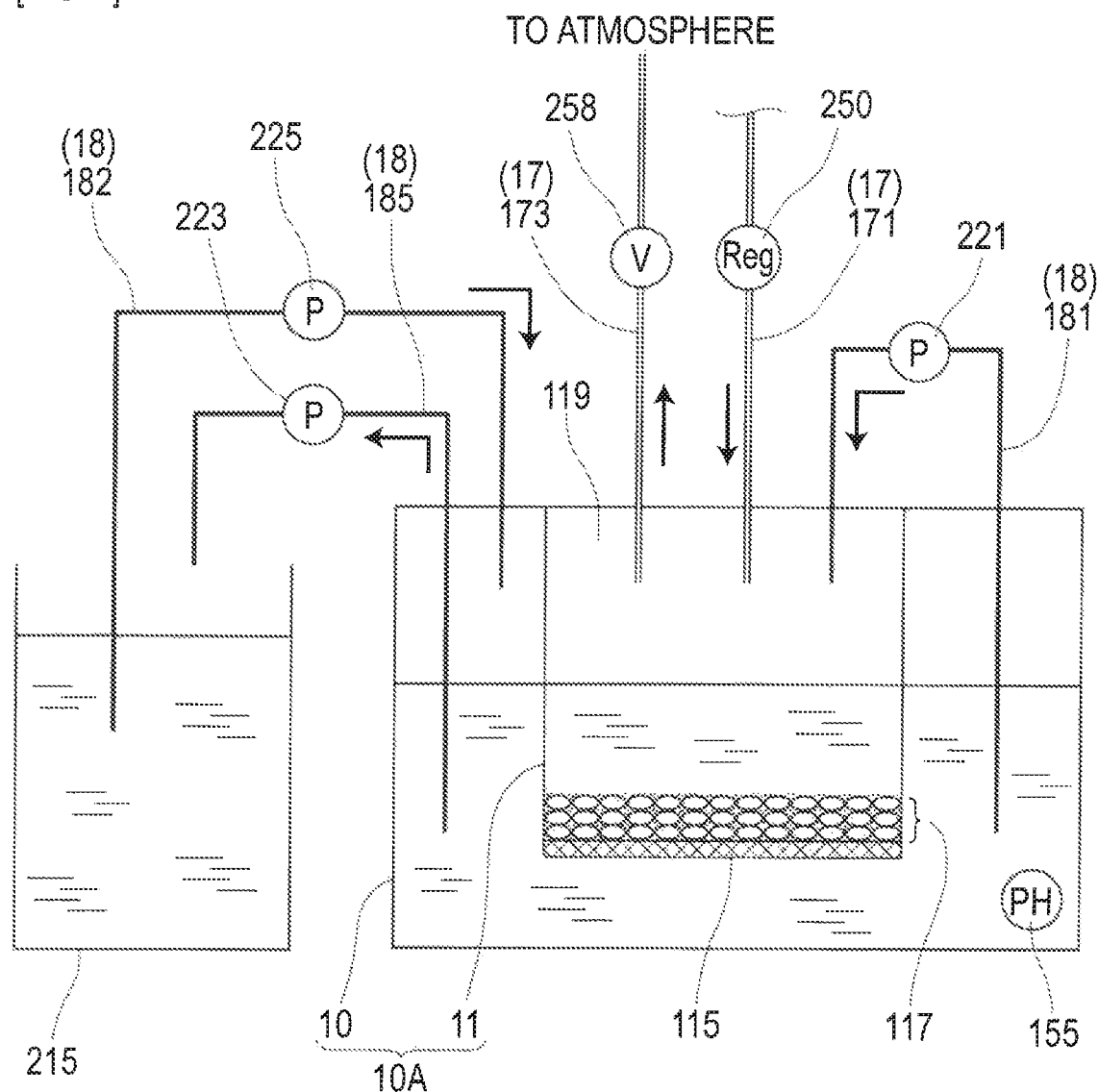
[FIG. 4]

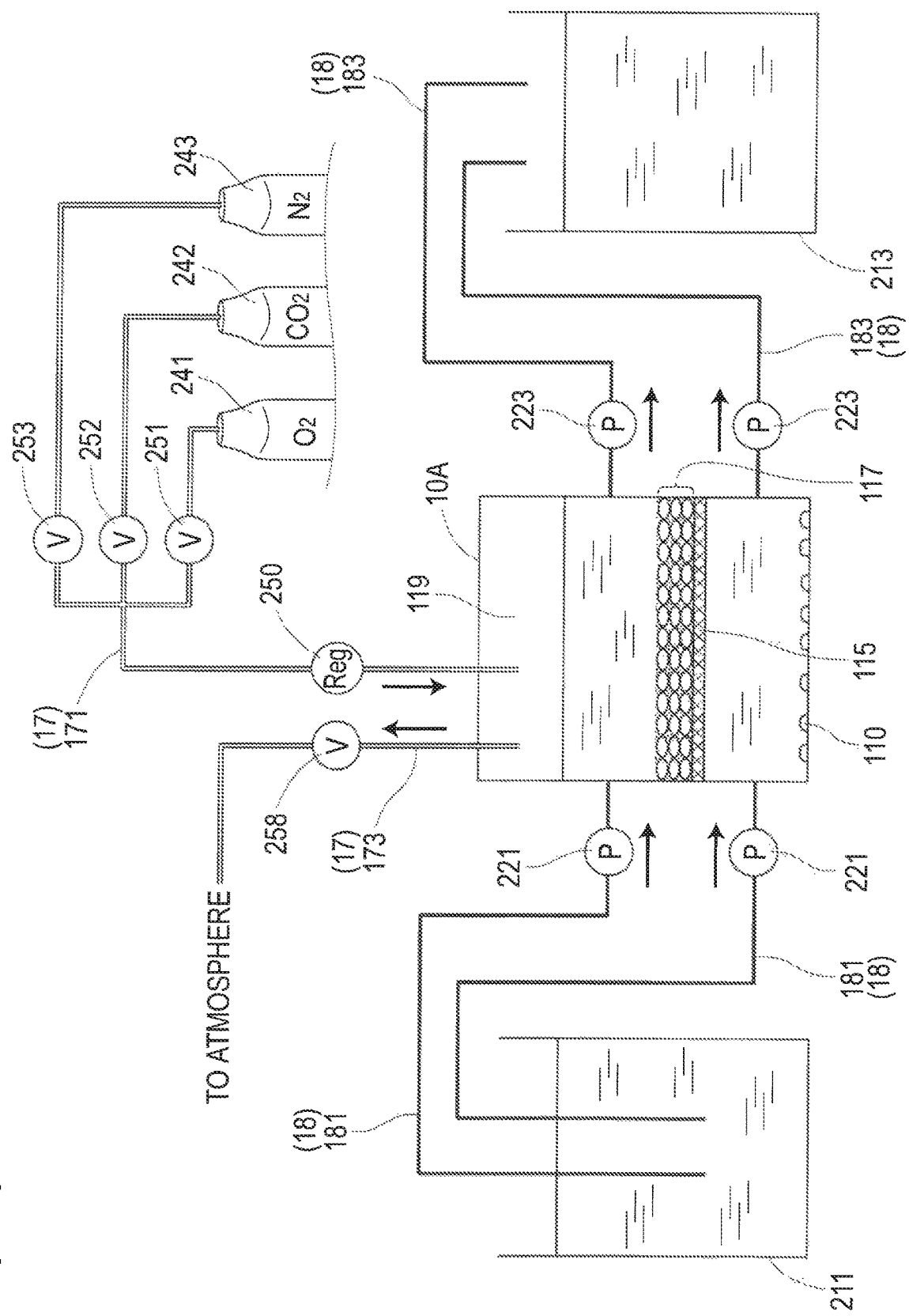
[FIG. 5]

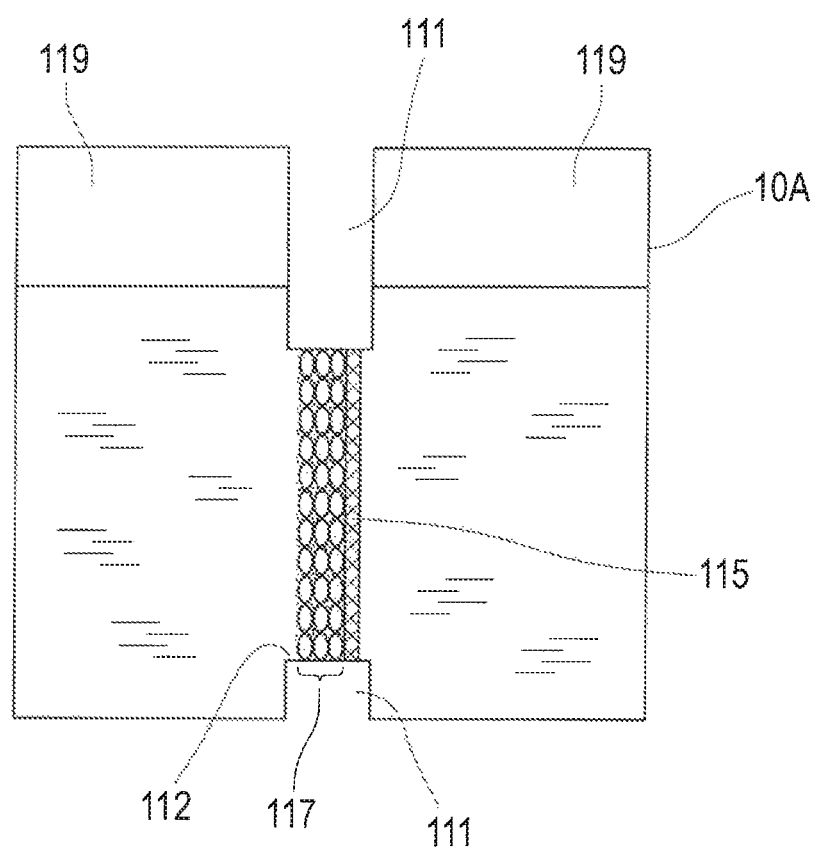
[FIG. 6]

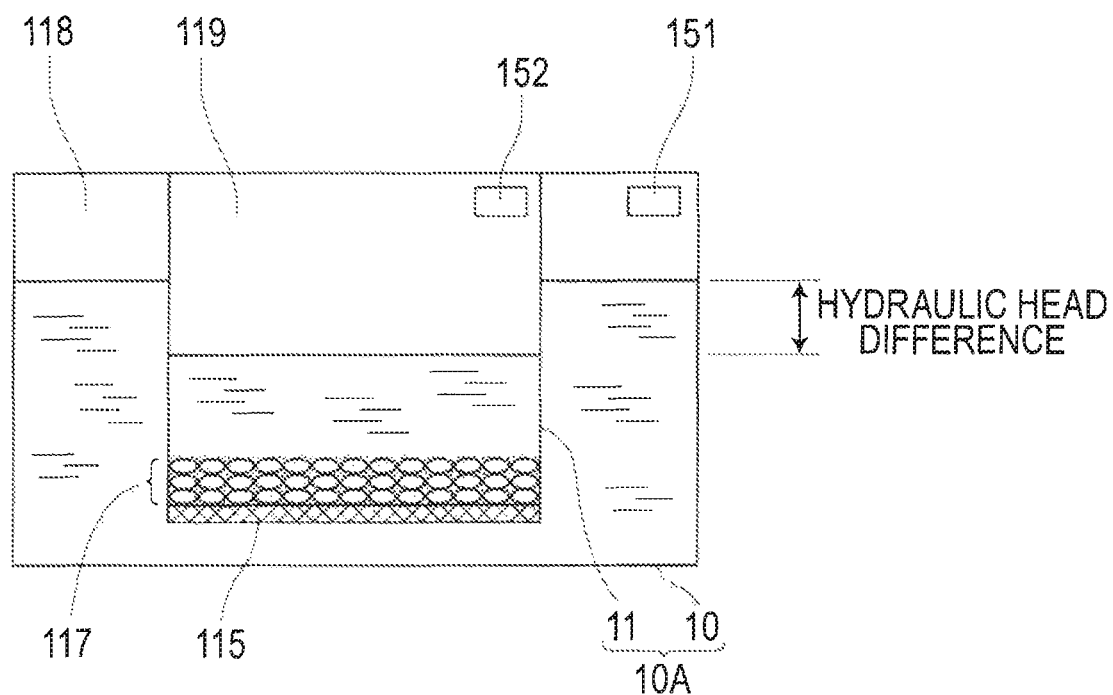
[FIG. 7]

PERFUSION CULTURE APPARATUS AND PERFUSION CULTURE METHOD

BACKGROUND OF THE INVENTION

Field of the Invention

The present invention relates to cell culture including, for example, culture of cells and biological tissue and other materials.

Description of the Related Art

Studies directed to practical use of an iPS cell, an ES cell, and other cells have been underway. One purpose of the studies is to achieve regenerative medicine in which cells are cultured and the cultured product is implanted in a person. A key factor that determines the success or failure of such regenerative medicine lies in reliability and precision of culture of cells and other biological materials. In culture so performed that cells are seeded in a culture vessel filled with a liquid medium, appropriately replacing the liquid medium allows improvement in the precision of the culture.

For example, Japanese Patent Laid-Open No. 2008-86264 proposes a culture apparatus that automatically replaces the liquid medium in a culture vessel. The culture apparatus achieves the liquid medium replacement by supplying a fresh liquid medium while discharging the liquid medium in the culture vessel having a hermetic structure with a pump. The culture apparatus allows automatic replacement of the liquid medium in the culture vessel and therefore reduction in the burden of liquid medium replacement work.

SUMMARY OF THE INVENTION

The culture apparatus of related art described above, however, has the following problem. That is, since the culture apparatus employs a culture vessel in which cells are so seeded as to be attached to the bottom surface of the vessel, a relatively sufficient liquid medium can be supplied to the front side of the cells, whereas the liquid medium supplied to the inside between the cells could be insufficient even with appropriate liquid medium replacement, and the technique of related art is undesirably inappropriate for tissue culture in which cells have a multilayer structure.

The present invention has been made in view of the problem of related art and provides a perfusion culture apparatus and a perfusion culture method capable of culturing cells having a multilayer structure.

An aspect of the present invention relates to a perfusion culture method including holding cells on a sheet-shaped carrier that allows passage of a liquid medium and holding the carrier in a state in which the liquid medium contacts with either of front and/or rear surfaces of the sheet-shaped carrier, and applying pressure from outside to either side of front and/or rear surfaces of the sheet-shaped carrier to create a pressure difference between the front and rear sides of the sheet-shaped carrier, and the pressure difference allows the liquid medium to pass through the sheet-shaped carrier.

Another aspect of the present invention relates to a perfusion culture apparatus including a sheet-shaped carrier that holds cells in a state in which a liquid medium is allowed to pass through the sheet-shaped carrier, and a vessel that holds the sheet-shaped carrier in a state in which the liquid medium contacts with either of front and/or rear surfaces of the sheet-shaped carrier, and pressure is applied from outside to either side of front and/or rear surfaces of the sheet-shaped carrier to create a pressure difference between the front and rear sides of the sheet-shaped carrier, and the liquid medium passes through the sheet-shaped carrier in accordance with the pressure difference.

Advantageous Effects of the Invention

In the perfusion culture method and the perfusion culture apparatus according to the present invention, a pressure difference between the opposite sides (front and rear sides) of the sheet-shaped carrier is created, and the liquid medium passes through the sheet-shaped carrier in accordance with the pressure difference. In the perfusion culture method and the like, the liquid medium can be supplied in the direction in which the liquid medium passes through cells held by the sheet-shaped carrier. Therefore, in a case where cells having a multilayer structure are cultured, for example, the liquid medium can be supplied to the cells in a lower layer and an intermediate layer with high reliability.

The perfusion culture method according to the present invention are thus a culture method having excellent characteristics that allow culture of cells having a multilayer structure, and the perfusion culture apparatus according to the present invention are thus a culture apparatus having excellent characteristics that allow culture of cells having a multilayer structure.

BRIEF DESCRIPTION OF THE DRAWINGS

FIG. 1 is a perspective view showing a perfusion culture apparatus;

FIG. 2 describes a perfusion culture method;

FIG. 3 is a block diagram showing an electrical configuration of the perfusion culture apparatus;

FIG. 4 is a descriptive diagram showing part of the configuration of another perfusion culture apparatus;

FIG. 5 is a descriptive diagram showing part of the configuration of another perfusion culture apparatus;

FIG. 6 is a descriptive diagram showing part of the configuration of another perfusion culture apparatus; and FIG. 7 describes a hydraulic head difference between a liquid medium in a culture vessel and a liquid medium in a well.

DETAILED DESCRIPTION OF THE PREFERRED EMBODIMENTS

In the present invention, the meaning of holding cells on the sheet-shaped carrier includes an aspect in which the sheet-shaped carrier directly holds the cells, an aspect in which the sheet-shaped carrier holds a scaffold material that directly holds cells, such as collagen and agar, so that the sheet-shaped carrier indirectly holds the cells with another member, such as the scaffold material, interposed between the cells and the sheet-shaped carrier, and other aspects.

Examples of the method for applying pressure from outside to at least the side of one of the front and rear surfaces of the sheet-shaped carrier include a method for applying pressure from outside to the liquid medium in contact with the one surface and a method for applying pressure from outside to a gas in contact with the one surface, and other methods.

In the present invention, the liquid medium may be in contact with only one of the front and rear surfaces of the sheet-shaped carrier or both the front and rear surfaces. In the case where the liquid medium is in contact with only one of the front and rear surfaces, the pressure is preferably applied from outside to the liquid medium in contact with the one surface. For example, in a case where the configuration in which collagen, agar, or any other scaffold material that holds cells is used and the sheet-shaped carrier holds the scaffold material is employed, the configuration in which the liquid medium is in contact with only one of the front and rear surfaces of the sheet-shaped carrier can be employed. In culture employing the configuration, the liquid medium drops through the sheet-shaped carrier's surface of the side that is not in contact the liquid medium. Further, in the case where the configuration in which the liquid medium is in contact with only one of the front and rear surfaces of the sheet-shaped carrier is employed, the pressure difference may instead be formed, for example, by application of negative pressure to the side of the other surface that is not in contact with the liquid medium.

In the perfusion culture method according to the present invention, it is preferable that the pressure difference is changed by changing a magnitude of the pressure applied from the outside periodically. For example, when the pressure difference is changed in a cycle close to the cycle of the heartbeat, culture in an environment closer to the biological environment can be performed.

It is also preferable that liquid media having different components contact with the front and rear surfaces of the sheet-shaped carrier, and that alternately changing direction of the pressure gradient in the passing through direction of the sheet-shaped carrier. This method is appropriate, for example, for culture of cells or tissue such as those of the kidney that have one side facing the blood and the other side facing the urine. For example, feeder cells that work in cooperation with cells when the cells proliferate or divide may be contained in one of the liquid media. In this case, two types of cells having different characteristics can be efficiently cultured on opposite sides of the sheet-shaped carrier.

It is also preferable that a vessel in a perfusion culture apparatus according to the present invention includes a culture vessel having a sheet-shaped carrier which forms at least part of outer surface and an accommodation vessel which is capable to accommodate the culture vessel, and that the pressure difference is formed by applying pressure from the outside to an inner side of either of the accommodation vessel and/or the culture vessel. In this case, the relatively simple configuration in which the accommodation vessel accommodates the culture vessel allows formation of the perfusion culture apparatus that cultures cells in a liquid medium that passes through the sheet-shaped carrier.

It is also preferable that either of the culture vessel and/or the accommodation vessel is provided with a liquid surface height detecting section that detects a liquid surface height of the liquid medium stored in the vessel. In this case, the liquid surface height of the liquid medium stored in the vessel is readily managed. The liquid surface height detecting section may be configured to detect whether or not the liquid surface height has reached a predetermined height or may be configured to detect the liquid surface height by measuring the distance to the liquid surface.

It is also preferable that the liquid medium is in contact with both the front and rear surfaces of the sheet-shaped carrier, and that the perfusion culture apparatus further includes means for controlling a hydraulic head difference that is the difference between the liquid surface height of the liquid medium stored in the culture vessel and the liquid surface height of the liquid medium stored in the accommodation vessel. Controlling the hydraulic head difference allows control of a liquid pressure component produced by the hydraulic head difference and applied to the sheet-shaped carrier. For example, causing the hydraulic head difference to be zero allows the liquid pressure component produced by the hydraulic head difference and applied to the sheet-shaped carrier to be reduced to nearly zero. Further, in this case, nearly 100% of the liquid pressure applied to the sheet-shaped carrier is produced by the pressure applied from outside to the liquid medium, whereby the liquid pressure applied to the sheet-shaped carrier is, for example, readily adjusted.

It is also preferable that pressure is applied from outside to the liquid medium in one of the accommodation vessel and the culture vessel while the liquid medium in the other vessel is set to have a positive hydraulic head difference. In this case, when the pressure difference described above is positive, the liquid pressure acting from the side of the one liquid medium toward the other liquid medium can be applied to the sheet-shaped carrier. When the pressure difference described above is zero, the liquid pressure acting from the side of the other liquid medium toward the one liquid medium can be applied to the sheet-shaped carrier depending on the hydraulic head difference. When the hydraulic head difference is set as described above, the direction of the liquid pressure applied to the sheet-shaped carrier can be reversed without reversing the direction of the pressure difference described above between positive and negative.

It is also preferable that the perfusion culture apparatus includes a gas chamber that allowed to be filled with a gas, and that the pressure difference described above is formed by applying gas pressure that fills the gas chamber to the liquid medium. In the case where pressure is applied via the gas, the pressure can be applied to the liquid medium in a nearly uniform manner. When the pressure is applied to the liquid medium in a nearly uniform manner, a situation in which an abrupt flow occurs in the liquid medium can be avoided, whereby a concern about excessive stimulus to the cells can be suppressed. Suppression of excessive stimulus to the cells allows improvement in the reliability and precision of the culture. The gas chamber may be a gas chamber having a hermetic structure or a gas chamber that has an inlet and an outlet and produces the pressure described above by using pressure loss produced when the gas flows.

Embodiments

The embodiment of the present invention will be specifically described with reference to the following embodiments;

First Embodiment

The present embodiment relates to a perfusion culture apparatus 1 capable of producing flow of a liquid medium in the direction in which the liquid medium passes cells under culture and a cell culture method using the perfusion culture apparatus 1. The contents of the perfusion culture apparatus 1 and the cell culture method will be described with reference to FIGS. 1 to 7.

The perfusion culture apparatus 1 is a unified apparatus including six wells (accommodation vessels) 10, each of which accommodates a culture vessel 11, a pool 211, which stores a fresh liquid medium (culture liquid), a pool 213, which collects a used liquid medium, gas cylinders 24, each of which stores a gas for applying pressure from outside to the liquid medium, and other components with the portions described above neatly arranged, as shown in FIG. 1.

The perfusion culture apparatus 1 is provided with pumps 221, which supply the culture vessels 11 with the liquid medium in the pool 211, pumps 223, which collect the liquid medium in the wells 10 into the pool 213, valves 251 to 253 (FIG. 2) and regulators 250 (FIG. 2), which control the gases in the gas cylinders 24, and other components, and a control unit 100 (FIG. 3), which controls the overall action of the perfusion culture apparatus 1, is further incorporated in the perfusion culture apparatus 1.

The perfusion culture apparatus 1 can operate alone in accordance, for example, with an action program incorporated in the control unit 100 in advance. For example, the perfusion culture apparatus 1 can be used in a condition in which it is accommodated in an incubator that as not shown but is managed in terms of temperature, humidity, concentration of carbonic acid gas, and other factors, and the perfusion culture apparatus 1 can therefore perform cell culture.

The perfusion culture apparatus 1 is an apparatus that is the combination of a case 14, which is provided, for example, with recesses that form the wells 10 and the pools 21 and a space that accommodates the gas cylinders 24, and a top plate 13. The top plate 13 has holes that allow the pumps 22 to be so disposed that upper portions of the pumps 22 pass through the holes and further includes hermetic gaskets 130, 131, and 135, which seal the wells 10, the pools 21, and other components. Further, in the top plate 13 are built or formed tubes that are not shown but connect the wells 10 to the pumps 22, tubes that are not shown but connect the pumps 22 to the pools 21, tubes that are not shown, but extend from the gas cylinders 24 to the wells 10, and other tubes.

The top plate 13 is attached to the case 14, for example, by screw fastening, so that the wells 10, the culture vessels 11, the pool s 21, and other components can be sealed with the hermetic gaskets 130, 131, and 135. Further, the top plate 13 is combined with the case 14 so that the tubes in the case 14 can be connected to the tubes in the top plate 13, whereby paths (reference characters 18 and 17 in FIG. 2) for the liquid medium and gas necessary for the action of the perfusion culture apparatus 1 can be ensured. The top plate 13 may, for example, have a double-layer structure formed of a top plate and an intermediate plate. For example, the top plate is layered on the intermediate plate in which grooves that form tubes are engraved in the front surface of the plate, so that the grooves can be used to form the paths of the tubes for the liquid medium, the gases, and other components.

The wells 10 are outer vessels that accommodate the cup-shaped culture vessels 11, as shown in FIGS. 1 and 2. Each of the wells 10 has a scaffold that is not shown but holds the culture vessel 11 and can fix the culture vessel 11 with a gap provided below the culture vessel 11. To allow the culture vessels 11 and the wells 10 to be simultaneously sealed with the hermetic gaskets 130 and 131 when the top plate 13 is combined with the case 14, the height and other dimensions of the culture vessels 11 and the wells 10 are so set that the openings thereof are flush with one another.

The culture vessels 11 are each a cup-shaped vessel having a bottom surface formed of a porous film 115, which is an example of the sheet-shaped carrier on which cells are seeded (by which cells are held). The film 115 is formed, for example, of a membrane filter having a large number of minute holes having a diameter ranging from about 0.3 to 0.5 μm. The cells are configured in the form of a cell suspension layer 117, which is mixed with gel, and seeded on and held by the film 115 so that no clogging of the film 115 occurs. The film 115 may instead be so designed that a large number of holes having a diameter ranging from 1 to 10 μm or holes having a larger diameter of about 100 μm are formed so that the holes themselves do not serve as channel resistance. In this case, collagen or agar may, for example, be employed as the scaffold material that allows the cells to be seeded, and the scaffold material may be caused to fill the holes.

The culture vessels 11 each store the liquid medium and are accommodated in the wells 10, which each similarly store the liquid medium, as shown in FIGS. 1 and 2. In the perfusion culture apparatus 1 according to the present embodiment, the combination of the culture vessels 11 and the wells 10 form vessels 10A, each of which holds the film 115 with the liquid medium being in contact with the front and rear surfaces of the film 115, on which the cells have been seeded. In each of the vessels 10A, the liquid medium in the culture vessel 11 passes through the film 115 at the bottom and flows into the well 10. The film 115, which forms the bottom surface of the culture vessel 11, is so located as to be separate from the bottom surface of the well 10, so that a channel for the liquid medium having passed through the film 115 is ensured.

The wells 10 and the culture vessels 11 are each provided with liquid surface sensors (liquid surface height detecting section) 151 and 152, respectively, which optically sense the liquid surface height, shown in FIG. 2. The liquid surface sensors 151 and 152 are each a distance measuring sensor that is a combination of a one-dimensional PSD (position sensitive detector) element that outputs an electric signal having a magnitude according to a light reception position and a light emitting diode that emits infrared light. The light emitting diode is so disposed as to be shifted in the aforementioned one-dimensional direction of the PSD element. The liquid surface sensors 151 and 152 can measure the liquid surface height of the liquid medium in accordance, for example, with the magnitude of the electric signal outputted from the PSD element when the light emitting diode emits light.

In each of the culture vessels 11, the value measured with the liquid surface sensor 152 is used to control the liquid surface height of the liquid medium to a specified height, whereby a gas chamber 119 is formed between the liquid medium and the top plate 13. The gas chamber 119 is provided with a pressure sensor 153, which measures the pressure of the gas that fills the gas chamber 119, an $O_2$ sensor 154, which measures the oxygen concentration in the gas, and a variety of other sensors used to control the perfusion culture apparatus 1. A gas chamber 118 is formed in each of the wells 10, as the gas chamber 119 is formed in each of the culture vessels 11, and atmospheric-pressure, sterilized air is introduced into the gas chamber 118 via a path that is not shown.

As shown in FIG. 2, in the perfusion culture apparatus 1, liquid medium paths 18 are formed via which the fresh liquid medium in the pool 211 is supplied to the culture vessels 11 and the used liquid medium is collected into the pool 213 via the wells 10, and gas (gaseous matter) paths 17 are also formed which extend from the gas cylinders 24 via the culture vessels 11 (gas chambers 119) and are open to the atmosphere.

The liquid medium paths 18 are paths for perfusing the fresh liquid medium to the cells seeded on the films 115. The gas paths 17 are paths via which a gas for applying pressure to the liquid medium in the culture vessels 11 travels and fills the gas chambers 119.

The liquid medium paths 18 each includes a supply path 181, via which the fresh liquid medium in the pool 211 is supplied to the culture vessel 11, and a collection path 183, via which the used liquid medium in the well 10 is collected into the pool 213. The supply path 181 is provided with the supply pump 221, which sucks the liquid medium in the pool 211 via the supply path 181. The collection path 183 is provided with the collection pump 223, which sucks the liquid medium in the well 10 via the collection path 183. The liquid medium is supplied to or collected from the wells 10 and the culture vessels 11 via the independent paths in such a way that the liquid surface height and other factors can be individually adjusted.

The gas paths 17 are each formed of a delivery path 171, which extends from the gas cylinder 24, each of which is filled with a gas, to the gas chamber 119 in the culture vessel 11, and a discharge path 173, which extends from the gas chamber 119 and is open to the atmosphere. The gas cylinders 24 are formed of an oxygen cylinder 241, a carbon dioxide cylinder 242, and a nitrogen cylinder 243, and a mixed gas is supplied to the gas chambers 119. The mixed gas is delivered to or discharged from the gas chambers 119 via the independent paths, whereby the magnitudes of pressure in the gas chambers 119 can be individually adjusted.

Along each of the delivery paths 171, there are provided the valves 251 to 253, which correspond to the respective gas cylinders 241 to 243, the regulator 250, which lowers the pressure of a high-pressure gas that is the mixture of the gases in the gas cylinders 241 to 243 and supplies the lowered (decompressed) gas into the gas chamber 119, an air flow meter that is not shown, and other components. The gases in the gas cylinders 241 to 243 are mixed with one another at predetermined proportions under the control of the valves 251 to 253 into a mixed gas, the pressure of which is lowered by the regulator 250, and the mixed gas fills the gas chamber 119. The oxygen and the carbon dioxide in the mixed gas are components necessary for survival of the cells. The carbon dioxide has an effect of suppressing oxidization of the liquid medium, and an appropriate concentration of the carbon dioxide is typically 5%.

In the present embodiment, a regulator capable of adjusting the pressure to be lowered under external control is employed as each of the regulators 250. The mixed gas that is the mixture of the gases in the gas cylinders 241 to 243 is supplied to the gas chambers 119 with the pressure of the mixed gas lowered to a desired value by the regulators 250. In place of or in addition to each of the regulators 250, a compression pump may be so disposed that the pressure of the gas to be supplied to the gas chamber 119 can be changed as appropriate.

The discharge path 173 is provided with a release valve 258, which selects whether or not the gas in the gas chamber 119 in the culture vessel 11 is released to the atmosphere. The release valve 258 is so controlled as to be open as appropriate, for example, when the gas in the gas chamber 119 is replaced or when the internal pressure in the gas chamber 119 is adjusted. At the time of the gas replacement, the release valve may be switched to the open state, whereas at the time of the pressure adjustment, duty control in which the open state and the closed state are periodically repeated may, for example, be applied to the release valve 258. According to the duty control, changing the ratio of the proportion of the open state to one cycle to change the valve opening of the release valve 258 allows adjustment of the magnitude of pressure loss, whereby allowing control of the internal pressure in the gas chamber 119 and other operations. In the perfusion culture apparatus 1 of the present embodiment, the gas chambers 119, the gas cylinders 24, which supply the gas chambers 119 with the gases, the regulators 250, the release valves 258, and other components form pressure means for creating a pressure difference between the opposite sides of each of the films 115 by applying pressure from outside to the liquid medium.

The perfusion culture apparatus 1 is electrically configured with the control unit 100 serving as a core, as shown in FIG. 3. A variety of sensors for grasping the action state of the apparatus are connected to the control unit 100, and the pumps, the valves, and other components that are control targets are also connected to the control unit 100. The sensors include the liquid surface sensors 151 and 152 described above, the pressure sensor 153, which measures the pressure in each of the gas chambers 119, and the $O_2$ sensor 154, which measures the oxygen concentration in each of the gas chamber 119, and other sensors. The pumps include the supply pump 221 and the collection pump 223 described above, which are provided in each of the liquid medium paths 18, and the regulator 250 described above, which is provided in each of the gas paths 17, and other pumps. The valves include the valves 251 to 253 described above, which are provided in the gas paths 17, and the release valves 258 described above, and other valves.

A cell culture method using the perfusion culture apparatus 1 configured as described above will next be described in terms of (1) preparation and (2) operation.

(1) Preparation

To perform cell culture, cells to be cultured are first seeded on the film 115, which forms the bottom surface of the culture vessel 11 in each of the wells 10. At this point, the cells to be cultured may be prepared in the form of suspension, which may then be mixed with gel, and the mixture may then be seeded on the film 115, which forms the bottom surface of the culture vessel 11. Mixing the cell suspension with gel as described above can prevent clogging of the film 115.

After the wells 10 and the culture vessels 11 are each filled with a fresh liquid medium, and the supply pool 211 is filled with a fresh liquid medium for replacement, the top plate 13 is attached to the case 14. Once the top plate 13 is attached, the pools 21, the wells 10, the culture vessels 11, and other components can be sealed, and the tubes and other components in the top plate 13 can be connected to the tubes and other components in the case 14, whereby the liquid medium paths 18 and the gas paths 17 can be ensured, as described above.

The perfusion culture apparatus 1 having undergone the preparation described above may be accommodated in an incubator that is not shown but is managed in terms of temperature, humidity, concentration of carbonic acid gas, and other factors. Cell culture can be performed high reliability and precision in a stable environment in the incubator, (2) Operation The perfusion culture apparatus 1 is powered on, and a start button or any other component that is not shown is used to start the action of the perfusion culture apparatus 1. In response to the start of the action, the control unit 100 first switches the state of the release valves 258 to the open state to allow the gas chambers 119 in the culture vessels 11 to be open to the atmosphere and controls the valves 251 to 253 in the delivery paths 171 and other components to supply the gas chambers 119 in the culture vessels 11 with the gases.

Supplying the gases with the release valves 258 in the discharge paths 173 open allows the air in the gas chambers 119 to be pushed out and the gas chambers 119 to be filled with the gases. The control unit 100 controls the opening of each of the three valves 251 to 253 to produce a mixed gas having predetermined gas component proportions, and the regulators 250 lower the pressure of the mixed gas to a predetermined value and supply the gas chambers 119 with the mixed gas.

The control unit 100, after it instructs supply of the gas the amount of which is necessary to push out the air in the gas chambers 119, switches the mode of the release valves 258 to a pressure control mode to control the release valves 258 in such a way that the pressure of the gas in the culture vessels 11 is equal to a specified value. In the cell culture, the valves 251 to 253 and the regulators 250 are so controlled that a predetermined amount of gas per unit time is supplied to the gas chambers 119, and the regulators 250, the release valves 256, and other components are so controlled that the pressure of the gas in the culture vessels 11 is equal to a specified value. The pressure of the gas is applied to the liquid surface of the liquid medium stored in each of the culture vessels 11 to pressurize the liquid surface, whereby the liquid pressure is applied to the film 115, on which the cells have been seeded. In the present embodiment, the specified pressure of the gas in the gas chambers 119 is set at 5 kPa. The difference between the pressure of the gas in each of the gas chambers 119 and the atmospheric pressure in the corresponding gas chamber 118 creates the pressure difference between the opposite sides of the film 115. The liquid pressure according to the pressure difference is applied to the film 115.

The control unit 100 causes the supply pumps 221 and the collection pumps 223 to act every predetermined period set in advance, for example, every 48 hours, in the culture to replace a fixed amount of liquid medium. In the liquid medium replacement, the supply pumps 221 are activated to supply the fresh liquid medium to the culture vessels 11, and the collection pumps 223 are activated to collect roughly the same amount of used liquid medium from the wells 10 into the pool 213. In the thus configured perfusion culture apparatus 1, the cells can be cultured with high reliability with the used old liquid medium replaced with the fresh liquid medium. In place of the replacement of the liquid medium every predetermined period, the liquid medium may be continuously replaced at a flow rate low enough not to stimulate the cells.

The control unit 100 drives the supply pump 221 in such a way that the liquid surface height of the liquid medium in each of the culture vessels 11 is equal to a specified height and drives the collection pump 223 in such a way that the liquid surface height of the liquid medium in each of the wells 10 is equal to the liquid surface height of the liquid medium in the corresponding culture vessel 11. Causing the culture vessels 11 and the wells 10 to have the same liquid surface height allows elimination of a hydraulic head difference of the liquid medium. Elimination of the hydraulic head difference allows a component of the liquid pressure of the liquid medium applied to the film 115, resulting from the pressure of the gas in each of the gas chambers 119 to approach 100%, whereby the liquid pressure is readily managed.

As described above, when cells are cultured by the operation of the perfusion culture apparatus 1 of the present embodiment, the liquid medium can be appropriately supplied to the cells seeded on the films 115, whereby the culture can be performed with high precision.

In the perfusion culture apparatus 1, in which the gas pressurizes the liquid medium in each of the culture vessels 11, the liquid pressure of the liquid medium can be applied to the cells seeded on the film 115 on the bottom surface of the culture vessel 11. When the liquid pressure of the liquid medium is applied in the direction in which the liquid medium passes through the film 115, a liquid medium flow that passes the cells seeded on the film 115 can be formed. The liquid medium can be supplied with high reliability, for example, even to cells in an intermediate layer or a lower layer of the multilayered cells, whereby necrosis and other undesirable phenomena of the cells in the inner layers can be avoided.

As described above, the perfusion culture apparatus 1 according to the present embodiment is a culture apparatus suitable for culture of tissue having a multilayer cell structure, and the perfusion culture method according to the present embodiment is a culture method suitable for culture of tissue having a multilayer cell structure.

For example, in a typical culture method of related art in which cells are stationarily placed and cultured on the bottom surface of a dish or any other vessel, a perfusion culture manner in which only supernatant liquid of a liquid medium is continuously replaced is likely not to be capable of supplying a sufficient amount of liquid medium to a deep portion of tissue or a cell mass. The culture method of related art is therefore likely not to sufficiently provide a period for which the cells can be maintained. Further, since cells intrinsically spread along the bottom surface, it is difficult for the culture method of related art to produce a liquid medium flow in the direction in which the liquid medium passes through the cells. The culture method of related art is therefore not suitable, for example, for culture of tissue having a multilayer cell structure.

On the other hand, in the culture method using the perfusion culture apparatus 1 according to the present embodiment, the films 115, each of which is a "sieve" having holes formed in the bottom surface of the film 115, is used to seed cells, and creating a pressure difference in the direction in which the liquid medium passes through the film 115 allows generation of a liquid medium flow in the direction in which the liquid medium passes through the cells. Generation of a liquid medium flow in the direction in which the liquid medium passes through the cells allows the liquid medium to be supplied to a deep portion of the cells or tissue, whereby the cells can be stably maintained for a long period.

For example, in the metabolism of hepatic cells, bile is unlikely to be normally produced unless a liquid medium is caused to flow sequentially through a layered cell structure formed of the following three cells: stellate cells, sinusoidal endothelial cells, and hepatic parenchymal cells layered in this order. However, when the liquid medium flows in the direction in which the liquid medium passes through the cells as described above, the culture can be performed in an environment closer to that of a living body (in vivo).

Further, pressurizing seeded cells allows generation of perfusion that supplies the liquid medium to a deep portion of even thick tissue with blood vessels, whereby culture can be performed under conditions closer to those of a living body. Controlling the applied pressure allows adjustment of the amount of liquid medium liquid passing through the tissue with blood vessels. The culture can therefore be performed under optimum conditions.

As described above, the perfusion culture apparatus 1 according to the present embodiment is a useful apparatus capable, for example, of construction of layered tissue formed of hepatic cells, construction of cancer cells having blood vessels, and application to skin tissue, iPS cells, and other pluripotent stem cells.

In the pressure difference between the side of the front surface and the side of the rear surface of each of the films 115 on which cells are seeded, allows adjustment of the liquid pressure and flow rate of the liquid medium passing through the cells. Fine adjustment of the liquid pressure and flow rate of the liquid medium allows an increase in the precision of the culture and hence improvement in the reliability thereof. In particular, in the perfusion culture apparatus 1, since relatively high liquid pressure can be applied to cells, a liquid medium can be supplied to relatively thick tissue having a thickness, for example, about 1 mm, and therefore having large passage resistance.

Collagen, agar, or any other substance is used as the scaffold material for seeding cells in some cases. In a case where agar, which has high passage resistance, is used as the scaffold material, the liquid medium is unlikely to pass through the scaffold material. On the other hand, according to the perfusion culture apparatus 1 according to the present embodiment, relatively high liquid pressure can be achieved by pressurizing the liquid medium from outside, whereby even in the case where a scaffold material having high passage resistance, such as agar, is employed, the liquid medium can pass through the scaffold material.

In the perfusion culture apparatus 1, adjustment of the pressure in the gas chamber 119 of each of the culture vessels 11 allows adjustment of the pressure difference between the opposite sides of the film 115, on which the cells have been seeded, whereby the liquid pressure applied to the film 115 can be controlled. For example, periodically increasing and decreasing the pressure in the gas chambers 119 allows pulsation for liquid pressure control that simulates heartbeats or blood pressure pulsation. The pressure control that causes pressure change that simulates blood pressure pulsation allows precise culture of cells under the influence of the blood pressure pulsation.

In the perfusion culture apparatus 1, the pressure in the gas chamber 118 of each of the wells 10 is set at the atmospheric pressure. For example, setting the pressure in the gas chamber 119 in each of the culture vessels 11 at a negative value allows reverse of the direction of the liquid pressure (direction of pressure gradient) applied to the film 115. As in the case of the gas chambers 119 of the culture vessels 11, the degree of hermeticity of the gas chambers 118 may be increased, and the gas chamber 118 may be filled with a gas. Setting the pressure in the gas chambers 118 to be higher than the pressure in the gas chambers 119 or vice versa allows changing the direction of the pressure gradient in the direction passing through the film 115, whereby the direction in which the liquid pressure is applied to the films 115 can be readily changed.

In place of the liquid medium paths 18 in FIG. 2, the liquid medium paths 18 shown in FIG. 4 may be employed. The liquid medium paths 18 shown in FIG. 4 are so configured that the liquid medium in each of the wells 10 is perfused via the supply path 181 into the culture vessel 11. For example, in a case where a decrease in pH in the liquid medium in a well 10 is detected with a pH sensor 155, a fresh liquid medium is supplied from a pool 215 via a path 182 into the well 10, and the same amount of liquid medium is collected via a path 185 into the pool 215.

Replacing the liquid medium with a fresh liquid medium whenever pH decreases as described above avoids oxidization of the liquid medium in the wells 10, whereby the properties of the liquid medium perfused to the culture vessels 11 can be maintained to some extent. Employing the configuration in which the liquid medium in the wells 10 is perfused into the culture vessels 11 allows reduction in consumption of the liquid medium, which is an expensive consumable material, whereby the culture cost can be reduced.

The perfusion culture apparatus may be so configured that the pressure difference between the opposite sides of each of the films 115, on which cells have been seeded, is created by disposing liquid media having different properties on the side of the front surface and the side of the rear surface of the film 115 and applying positive or negative pressure to one of the liquid media, as show in FIG. 5. In this apparatus, the film 115, which serves as a partition, is provided at an intermediate height of a sealable vessel 10A, and a liquid medium supply port and a liquid medium collection port are provided on each of the upper and lower sides of the film 115. Feeder cells 110, which diffuse a specific component in the liquid medium, are stationarily placed, for example, on the bottom surface of the vessel 103 and cause the properties of the liquid media on the upper and lower sides of the film 115 to differ from each other.

The space below the film 115 is so tight filled with the liquid medium that the liquid medium is in contact with the film 115, whereas in the space above the film 115, the liquid surface height of the liquid medium is adjusted to a specified height so that the gas chamber 119 is formed in the sealed vessel 10A. A gas path 17 is connected to the gas chamber 119. Adjustment of the pressure of the gas in the gas chamber 119 allows adjustment of the pressure applied to the liquid medium.

The pressure in the gas chamber 119 that is applied to the upper liquid medium may be positive pressure or negative pressure. In the case of positive pressure, the upper liquid medium can be supplied to the cells seeded on the film 115, whereas in the case of negative pressure, the lower liquid medium can be supplied to the cells. The thus configured apparatus is suitable for culture of cells having front and rear sides facing different body fluids or other substances, for example, kidney tissue having one side facing the blood and the other side facing the urine. The pressure in the gas chamber 119 can be so controlled that the direction of the pressure alternately changes with time between positive and negative.

Consider a vessel 10A having a partition 111 that divides the vessel 10A into right and left portions, as shown in FIG. 6, and gas chambers 119 may be provided on opposite sides of the film 115 disposed in a hole 112 of the partition 111. The pressure in each of the gas chambers 119 may be controlled, or the pressure in one of the gas chambers 119 may be controlled. In the case where the pressure in each of the gas chambers 119 is controlled, for example, the pressure in the gas chamber 119 on the left in FIG. 6 is set at a positive value, and the pressure in the gas chamber 119 on the right in FIG. 6 is set to be the atmospheric pressure, so that a pressure gradient can be so formed that the pressure decreases from left to right. Conversely, setting the pressure in the right gas chamber 119 at a positive value allows formation of a pressure gradient that causes the pressure to decrease in the opposite direction. Controlling the pressure in each of the right and left gas chambers 119 allows reverse of the direction of the pressure gradient without use of negative pressure.

The perfusion culture apparatus 1 includes the liquid surface sensors 151 and 152, which measure the height of the liquid surfaces in the culture vessels 11 and the wells 10. The liquid surface sensors 151 and 152, when combined with the supply pump 221 and the collection pump 223, form means for controlling the hydraulic head difference that is shown in FIG. 7 by way of example and is the difference between the liquid surface height of the liquid medium stored in the culture vessels 11 and the liquid surface height of the liquid medium stored in the wells 10. In FIG. 7, to clearly show the hydraulic head difference, the liquid surface heights are so drawn that they differ from each other. The hydraulic head difference control means including the liquid surface sensors 151 and 152 is not a configuration essential in the present invention. For example, after the culture vessels 11 and the wells 10 are appropriately adjusted in the preparation described above, the liquid surface heights in the culture vessels 11 and the wells 10 can be appropriately maintained in the culture by controlling the supply pumps 221 and the collection pumps 223 in such a way that the amount of liquid medium supplied to the culture vessels 11 is equal to the amount of liquid medium collected from the wells 10. Further, in the present embodiment, the hydraulic head difference between the liquid medium in the culture vessels 11 and the liquid medium in the wells 10 is controlled to be zero, but causing the hydraulic head difference to be zero is not essential, and a hydraulic head difference may occur or change to some extent in the culture, and the hydraulic head difference may be controlled to be a predetermined value.

The liquid surface sensors 151 and 152, which are used as the means for controlling the hydraulic head difference, are also useful as means for avoiding a trouble of spillover of the liquid medium out of the culture vessels 11 or the wells 10.

Specific examples of the present invention have been described above with reference to the embodiment. The specific examples merely disclose examples of the technology encompassed in the claims. Needless to say, the claims should not be read in a limited sense by the configurations, numerals, and other factors in the specific examples. The claims encompass technologies of a variety of modifications, changes, or appropriate combinations of the specific examples described above, for example, by using known technologies and knowledge of a person skilled in the art.

What is claimed is:

1. A perfusion culture method comprising:
providing a device that includes a vessel holding a sheet-shaped carrier on which cells are held and that allows passage of a liquid medium, the sheet-shaped carrier being held in a state in which the liquid medium contacts at least one of front and rear surfaces of the sheet-shaped carrier, and the vessel having a gas chamber (i) that is in contact with a liquid surface of the liquid medium facing one of the front and rear surfaces of the sheet-shaped carrier and (ii) that is hermetically separated from a space generated on a side facing the other of the front and rear surfaces of the sheet-shaped carrier; and
creating a pressure difference between opposite sides of the sheet-shaped carrier, thereby causing the liquid medium to pass through the sheet-shaped carrier in accordance with the pressure difference, by adjusting internal pressure of the gas chamber so that liquid pressure of the liquid medium applied to the one of the front and rear surfaces of the sheet-shaped carrier is adjusted.

2. The perfusion culture method according to claim 1, wherein the adjusting of the internal pressure of the gas chamber comprises periodically changing a magnitude of the internal pressure of the gas chamber so that the pressure difference is periodically changed.

3. The perfusion culture method according to claim 2, wherein the liquid medium is in contact with both the front and rear surfaces of the sheet-shaped carrier, and wherein the method further comprises controlling a hydraulic head difference, which is a difference between liquid surface heights of the liquid medium at the front and rear surfaces of the sheet-shaped carrier, to be zero.

4. The perfusion culture method according to claim 2, wherein the liquid medium is in contact with both the front and rear surfaces of the sheet-shaped carrier, and wherein the internal pressure of the gas chamber is adjusted so that a high pressure side and a low pressure side of the front and rear sides of the sheet-shaped carrier are alternately changed.

5. The perfusion culture method according to claim 4, wherein the liquid medium is in contact with both the front and rear surfaces of the sheet-shaped carrier, and wherein the method further comprises controlling a hydraulic head difference, which is a difference between liquid surface heights of the liquid medium at the front and rear surfaces of the sheet-shaped carrier, to be zero.

6. The perfusion culture method according to claim 1, wherein the liquid medium is in contact with both the front and rear surfaces of the sheet-shaped carrier, and wherein the internal pressure of the gas chamber is adjusted so that a high pressure side and a low pressure side of the front and rear sides of the sheet-shaped carrier are alternately changed.

7. The perfusion culture method according to claim 6, wherein the liquid medium is in contact with both the front and rear surfaces of the sheet-shaped carrier, and wherein the method further comprises controlling a hydraulic head difference, which is a difference between liquid surface heights of the liquid medium at the front and rear surfaces of the sheet-shaped carrier, to be zero.

8. The perfusion culture method according to claim 1, wherein the liquid medium is in contact with both the front and rear surfaces of the sheet-shaped carrier, and wherein the method further comprises controlling a hydraulic head difference, which is a difference between liquid surface heights of the liquid medium at the front and rear surfaces of the sheet-shaped carrier, to be zero.

* * * * *